(12) United States Patent
Ye et al.

(10) Patent No.: US 10,638,951 B2
(45) Date of Patent: May 5, 2020

(54) SYSTEMS AND METHODS FOR MAGNETIC RESONANCE IMAGING

(71) Applicant: SHANGHAI UNITED IMAGING HEALTHCARE CO., LTD., Shanghai (CN)

(72) Inventors: Yongquan Ye, Houston, TX (US); Jinguang Zong, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 16/231,721

(22) Filed: Dec. 24, 2018

(65) Prior Publication Data

US 2020/0008701 A1    Jan. 9, 2020

(30) Foreign Application Priority Data

Jul. 6, 2018    (CN) .......................... 2018 1 0737109

(51) Int. Cl.
| | | |
|---|---|---|
| G01V 3/00 | (2006.01) | |
| A61B 5/055 | (2006.01) | |
| G01R 33/385 | (2006.01) | |
| G01R 33/24 | (2006.01) | |
| G01R 33/54 | (2006.01) | |
| G01R 33/44 | (2006.01) | |

(52) U.S. Cl.
CPC ............ *A61B 5/055* (2013.01); *G01R 33/243* (2013.01); *G01R 33/385* (2013.01); *G01R 33/443* (2013.01); *G01R 33/54* (2013.01)

(58) Field of Classification Search
USPC .......................................................... 324/307
See application file for complete search history.

(56) References Cited

U.S. PATENT DOCUMENTS

| | | | |
|---|---|---|---|
| 8,781,197 B2 | 7/2014 | Wang et al. | |
| 9,165,386 B2 * | 10/2015 | Sato ...................... | A61B 5/055 |
| 9,448,289 B2 | 9/2016 | Wang et al. | |

(Continued)

OTHER PUBLICATIONS

E. Mark Haacke et al., Quantitative Susceptibility Mapping: Current Status and Future Directions. Magnetic Resonance Imaging, 33(1): 1-25, 2015.

(Continued)

*Primary Examiner* — Rodney E Fuller
(74) *Attorney, Agent, or Firm* — Metis IP LLC

(57) ABSTRACT

A method may include obtaining first image data of a first subject and obtaining a target machine learning model. The first image data may indicate a first intensity distribution of a first magnetic field relative to at least one portion of the first subject. The target machine learning model may provide a mapping relationship between second intensity distributions of second magnetic fields and corresponding second susceptibility distributions associated with second subjects under the second magnetic fields. The method may also include generating a first susceptibility distribution associated with the first subject under the first magnetic field based on the target machine learning model and the first image data. The method may further include determining a target MR image of the at least one portion of the first subject based on the first susceptibility distribution.

20 Claims, 11 Drawing Sheets

(56) References Cited

U.S. PATENT DOCUMENTS

| | | | | |
|---|---|---|---|---|
| 2004/0032261 | A1* | 2/2004 | Schweikard | G01R 33/56527 |
| | | | | 324/309 |
| 2015/0145514 | A1* | 5/2015 | Sharma | G01R 33/243 |
| | | | | 324/309 |
| 2017/0097399 | A1* | 4/2017 | Shiodera | G06T 7/0012 |
| 2019/0076049 | A1* | 3/2019 | Satoh | G01R 33/56 |
| 2019/0261906 | A1* | 8/2019 | Shirai | G01R 33/5608 |
| 2019/0318511 | A1* | 10/2019 | Ye | G06K 9/6202 |

OTHER PUBLICATIONS

Chunlei Liu et al., Quantitative Susceptibility Mapping: Contrast Mechanisms and Clinical Applications. Tomography, 1(1): 3-17, 2015.

Wang Yi et al., Quantitative Susceptibility Mapping (QSM): Decoding MRI Data for a Tissue Magnetic Biomarker. Magnetic Resonance in Medicine, 73(1): 82-101, 2015.

Christian Langkammer et al., Quantitative Susceptibility Mapping: Report from the 2016 Reconstruction Challenge, Magnetic Resonance in Medicine, 2017.

Akshay S. Chaudhar et al., Super-resolution Musculoskeletal MRI Using Deep Learning, Magnetic Resonance in Medicine, 2139-2154, 2018.

Vladimir Golkov et al., q-Space Deep Learning for Twelve-Fold Shorter and Model-Free Diffusion MRI Scans, IEEE Transaction on Mededical Imaging, 35(5): 1344-1351, 2016.

Zhiqiong Wang et al., Single NMR Image Super-resolution Based on Extreme Learning Machine, Physica Medica, 32(10): 1331-1338, 2016.

* cited by examiner

600

```
┌─────────────────────────────────────────────────┐
│ Obtaining a plurality of first groups of training data associated │  602
│ with multiple first samples, each group of the plurality of       │
│ groups of training data including first image data and a          │
│ reference first susceptibility distribution associated with a first│
│ sample                                                             │
└─────────────────────────────────────────────────┘
                          ↓
┌─────────────────────────────────────────────────┐
│ Obtaining an objective function including a regularization │  604
│ configured to constrain the training of a machine learning │
│ model                                                       │
└─────────────────────────────────────────────────┘
                          ↓
┌─────────────────────────────────────────────────┐
│ Training the machine learning model using the plurality of first │  606
│ groups of training data based on the objective function to        │
│ obtain a first machine learning model                             │
└─────────────────────────────────────────────────┘
                          ↓
┌─────────────────────────────────────────────────┐
│ Obtaining a plurality of second groups of training data │  608
│ associated with a second sample, each group of the plurality │
│ of second groups of training data including second image      │
│ data and a second reference susceptibility distribution       │
└─────────────────────────────────────────────────┘
                          ↓
┌─────────────────────────────────────────────────┐
│ Training the first machine learning model using the plurality of │  610
│ second groups of training data based on the objective             │
│ function to obtain a second machine learning model                │
└─────────────────────────────────────────────────┘
                          ↓
┌─────────────────────────────────────────────────┐
│ Designating the second machine learning model as a target │  612
│ machine learning model                                      │
└─────────────────────────────────────────────────┘

┌─────────────────────────────────────────────────┐
│ Designating the first machine learning model as a target │  614
│ machine learning model                                     │
└─────────────────────────────────────────────────┘
```

FIG. 6

SYSTEMS AND METHODS FOR MAGNETIC RESONANCE IMAGING

CROSS-REFERENCE TO RELATED APPLICATIONS

This present application claims priority of Chinese Application No. 201810737109.1 filed on Jul. 6, 2018, the entire contents of which are incorporated herein by reference.

TECHNICAL FIELD

The disclosure generally relates to magnetic resonance imaging systems, and more particularly relates to systems and methods for quantitative susceptibility mapping (QSM).

BACKGROUND

Magnetic resonance imaging (MRI) is an exemplary medical imaging technique used in medical diagnose. Magnetic resonance (MR) scanners use strong magnetic fields, magnetic field gradients, and radio waves to generate images of an object to be scanned (e.g., tissues or organs in a body). QSM technique is widely used in MR imaging by determining a susceptibility distribution associated with the object. Using QSM technique, the intensity distribution of a magnetic field (i.e., field distribution) relative to at least one portion of the object may be determined based on MR imaging data, and the susceptibility distribution associated with the object under the magnetic field may be determined based on a physical relationship between susceptibility distribution and field distribution defined by a dipole kernel function. Generally, the susceptibility distribution associated with an object may be determined using a reverse dipole kernel function, which may cause artifacts in an MR image reconstructed based on the susceptibility distribution and poor image quality. Thus, it is desirable to provide systems and methods for reconstructing MR images based on susceptibility distribution with improved image quality.

SUMMARY

In an aspect of the present disclosure, a system for magnetic resonance imaging is provided. The system may include one or more scanners, at least one storage medium including a set of instructions for determining radiation dosimetry, and at least one processor configured to communicate with the at least one storage medium. When executing the set of instructions, the at least one processor may cause the system to perform following operations. The at least one processor may cause the system to obtain first image data of a first subject, the first image data indicating a first intensity distribution of a first magnetic field relative to at least one portion of the first subject. The at least one processor may also cause the system to obtain a target machine learning model that provides a mapping relationship between second intensity distributions of second magnetic fields and corresponding second susceptibility distributions associated with second subjects under the second magnetic fields. The at least one processor may further cause the system to generate a first susceptibility distribution associated with the first subject under the first magnetic field based on the target machine learning model and the first image data of the first subject. The at least one processor may further cause the system to determine a target MR image of the at least one portion of the first subject based on the first susceptibility distribution associated with the first subject.

In some embodiments, the first image data includes at least one of an MR complex diagram, an MR phase diagram, or an MR field diagram.

In some embodiments, to generate, based on the target machine learning model and the first image data of the first subject, a first susceptibility distribution associated with the first subject under the first magnetic field, the at least one processor is further configured to cause the system to perform following operations. The at least one processor may further cause the system to input the first image data of the first subject into the target machine learning model. The at least one processor may further cause the system to obtain the first susceptibility distribution associated with the first subject outputted by the target machine learning model based on the mapping relationship.

In some embodiments, to generate, based on the target machine learning model and the first image data of the first subject, a first susceptibility distribution associated with the first subject under the first magnetic field, the at least one processor is further configured to cause the system to cause the system to perform following operations. The at least one processor may further cause the system to identify the first intensity distribution of the first magnetic field from the first image data. The at least one processor may further cause the system to input the first intensity distribution of the first magnetic field into the target machine learning model. The at least one processor may further cause the system to obtain the first susceptibility distribution associated with the first subject outputted by the target machine learning model based on the mapping relationship.

In some embodiments, the at least one processor is further configured to cause the system to perform a domain transformation operation on at least one of the first image data of the first subject or the first susceptibility distribution associated with the first subject.

In some embodiments, the at least one processor is further configured to cause the system to perform following operations. The at least one processor may further cause the system to perform a first domain transformation operation on the first image data of the first subject. The at least one processor may further cause the system to perform a second domain transformation operation on the first susceptibility distribution associated with the first subject, the second domain transformation operation being a reverse operation of the first domain transformation operation.

In some embodiments, the at least one processor is further configured to cause the system to generate the first susceptibility distribution associated with the first subject based on the mapping relationship and at least one of a scanning parameter associated with the first image data, a dipole kernel function associated with the first image data, a feature relating to a reference subject around the first subject, a feature relating to the at least one portion of the first subject, or a spatial relationship between the first subject and the reference subject around the first subject.

In some embodiments, to obtain a target machine learning model, the at least one processor is further configured to cause the system to perform following operations. The at least one processor may further cause the system to obtain a plurality of first groups of training data, each group of the plurality of first groups of training data including second image data and a first reference susceptibility distribution associated with a third subject, the second image data indicating a third intensity distribution of a third magnetic field relative to the third subject. The at least one processor may further cause the system to train a machine learning model based on the plurality of first groups of training data to obtain a first machine learning model. The at least one processor may further cause the system to determine the target machine learning model based on the first machine learning model. In some embodiments, to train a machine learning model based on the plurality of first groups of training data, the at least one processor is further configured to cause the system to perform following operations. The at least one processor may further cause the system to identify, for each group of the plurality of first groups of training data, the third intensity distribution of the third magnetic field from the second image data. The at least one processor may further cause the system to train the machine learning model using the identified third intensity distribution of the third magnetic field and the first reference susceptibility distribution associated with the third subject corresponding to the each group of the plurality of first groups of training data.

In some embodiments, to determine the target machine learning model based on the first machine learning model, the at least one processor is further configured to cause the system to perform following operations. The at least one processor may further cause the system to obtain a plurality of second groups of training data, each group of the plurality of groups of training data including third image data and a second reference susceptibility distribution associated with the first subject. The at least one processor may further cause the system to train the first machine learning model using the plurality of second groups of training data to obtain a second machine learning model. The at least one processor may further cause the system to designate the second machine learning model as the target machine leaning model.

In some embodiments, to obtain a plurality of first groups of training data, the at least one processor is further configured to cause the system to perform following operations. The at least one processor may further cause the system to, for each of one or more groups of the plurality of first groups of training data, determine one or more first reference susceptibility distributions associated with the third subject. The at least one processor may further cause the system to simulate the second image data based on the corresponding first reference susceptibility distributions. The at least one processor may further cause the system to determine the one or more groups of the plurality of first groups of training data based on the one or more first reference susceptibility distributions and the simulated second image data.

In some embodiments, to train a machine learning model based on the plurality of first groups of training data, the at least one processor is further configured to cause the system to perform following operations. The at least one processor may further cause the system to obtain an objective function including a regularization configured to constrain the training of the machine learning model to converge the objective function. The at least one processor may further cause the system to perform a plurality of iterations based on the objective function using the plurality of first groups of training data.

In some embodiments, the regularization is constructed based on at least one of a scanning parameter associated with the second image data, a dipole kernel function associated with the second image data, a feature relating to a reference subject around the fourth subject, a feature relating to the at least one portion of the fourth subject, or a spatial relationship between the fourth subject and the reference subject around the fourth subject.

In another aspect of the present disclosure, a method for magnetic resonance imaging implemented on at least one device each of which has at least one processor and a storage device is provided. The method may include one or more of the following operations. The method may include obtaining first image data of a first subject, the first image data indicating a first intensity distribution of a first magnetic field relative to at least one portion of the first subject. The method may also include obtaining a target machine learning model that provides a mapping relationship between second intensity distributions of second magnetic fields and corresponding second susceptibility distributions associated with second subjects under the second magnetic fields. The method may further include generating a first susceptibility distribution associated with the first subject under the first magnetic field based on the target machine learning model and the first image data of the first subject. The method may further include determining a target MR image of the at least one portion of the first subject based on the first susceptibility distribution associated with the first subject.

In yet another aspect of the present disclosure, a non-transitory computer readable medium is provided. The non-transitory computer readable medium storing instructions, the instructions, when executed by a computer, may cause the computer to implement a method. The method may include one or more of the following operations. The method may include obtaining first image data of a first subject, the first image data indicating a first intensity distribution of a first magnetic field relative to at least one portion of the first subject. The method may also include obtaining a target machine learning model that provides a mapping relationship between second intensity distributions of second magnetic fields and corresponding second susceptibility distributions associated with second subjects under the second magnetic fields. The method may further include generating a first susceptibility distribution associated with the first subject under the first magnetic field based on the target machine learning model and the first image data of the first subject. The method may further include determining a target MR image of the at least one portion of the first subject based on the first susceptibility distribution associated with the first subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 is a flowchart illustrating an exemplary process for generating a target machine learning model for magnetic resonance imaging according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 3:
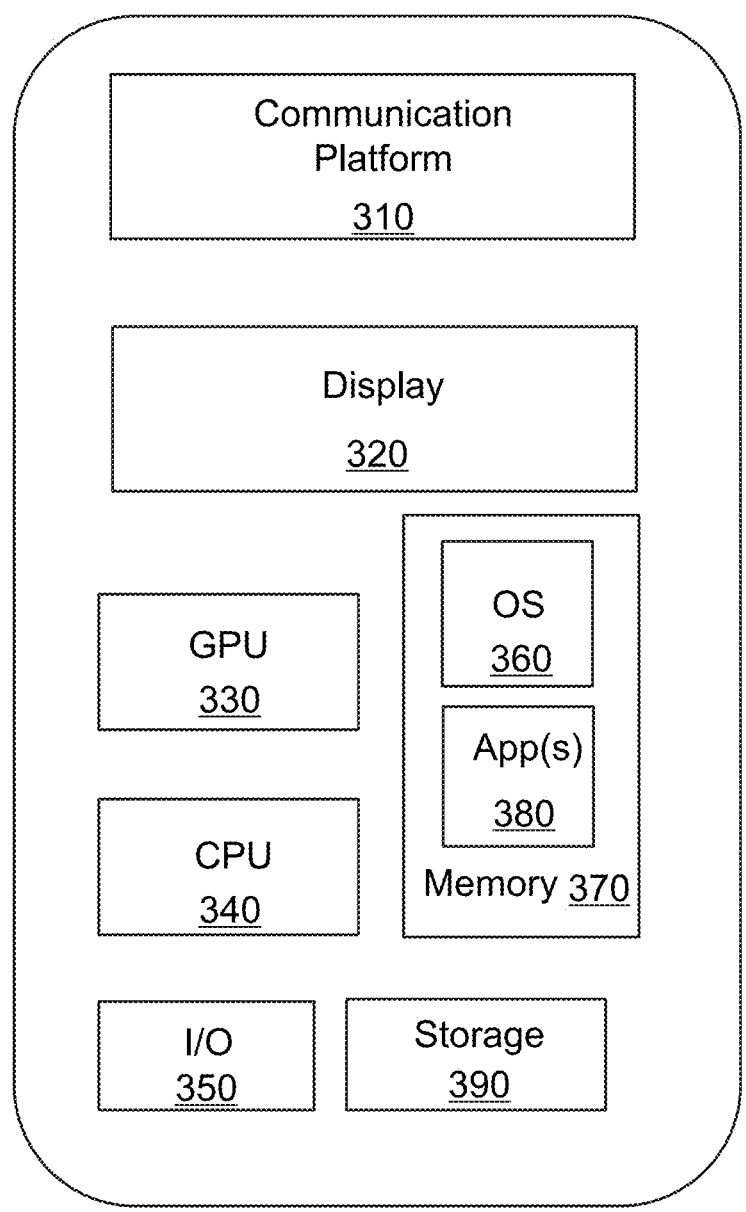
FIG. 3 is a schematic diagram illustrating hardware and/or software components of an exemplary mobile device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processing unit 320 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for magnetic resonance imaging. A system for magnetic resonance imaging may interact with an MR scanner to obtain and/or retrieve from a storage device MR image data. The system may include at least one storage device storing executable instructions, and at least one processor in communication with the at least one storage device. When executing the executable instructions, the at least one processor may cause the system to obtain image data of a subject (e.g., MR image data acquired by the MR scanner, retrieved from a storage device). The image data may indicate an intensity distribution of a magnetic field relative to at least one portion of the subject. The at least one processor may also cause the system to obtain a target machine learning model that provides a mapping relationship between second intensity distributions of magnetic fields and corresponding susceptibility distributions associated with subjects under the magnetic fields. The at least one processor may further cause the system to generate a susceptibility distribution associated with the subject under the magnetic field based on the target machine learning model and the image data of the subject, and determine a target MR image of the at least one portion of the subject based on the susceptibility distribution associated with the subject.

Accordingly, the system may generate susceptibility distribution associated with a subject directly by inputting image data of the subject into the target machine learning model, which may improve processing speed for generating the susceptibility distribution associated with a subject and may be applied in different clinical situations. In some embodiments, the system may update a plurality of training samples according to clinical demands and update the target machine learning model by training the target machine learning model using the updated plurality of training samples. Accordingly, the system may adapt to complex clinical situations and have improved robustness.

Figure 1:
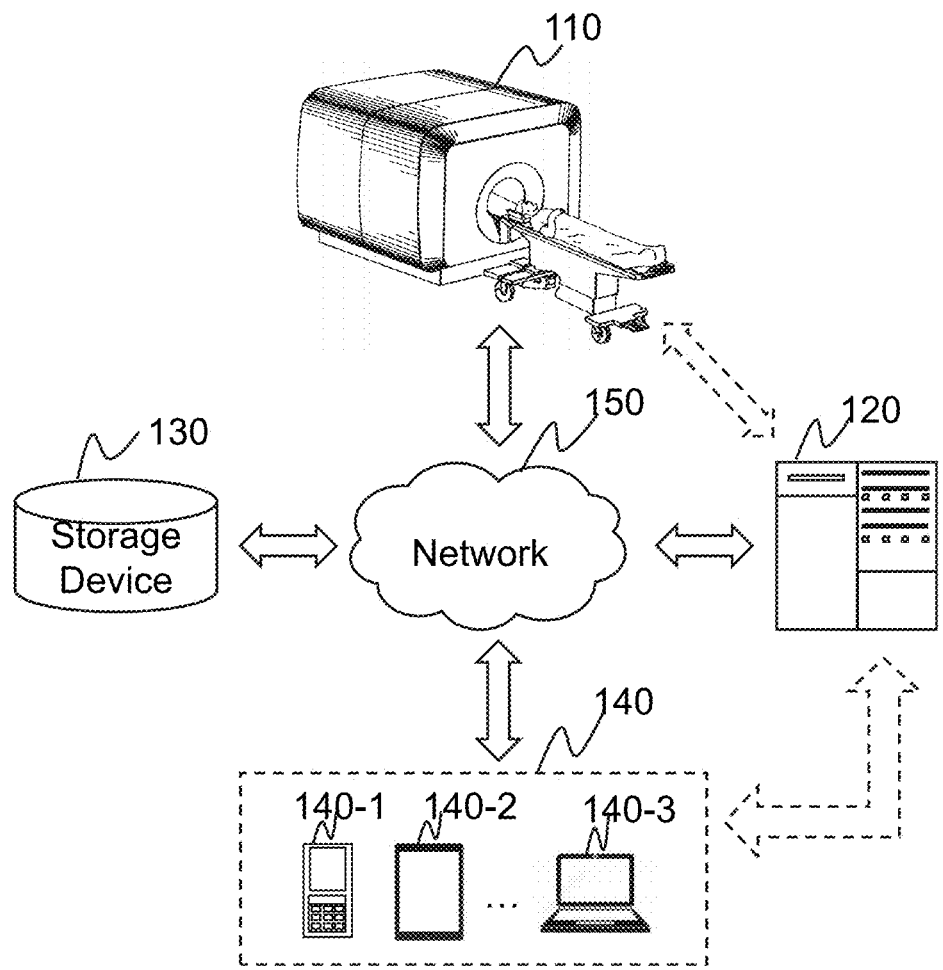
FIG. 1 is a schematic diagram illustrating an exemplary imaging system according to some embodiments of the present disclosure.

FIG. 1 is a schematic diagram illustrating an exemplary MRI system 100 according to some embodiments of the present disclosure. As illustrated, the MRI system 100 may include an MR scanner 110, a processing device 120, a storage device 130, one or more terminals 140, and a network 150. The components in the MRI system 100 may be connected in one or more of various ways. Merely by way of example, as illustrated in FIG. 1, the MR scanner 110 may be connected to the processing device 120 through the network 150. As another example, the MR scanner 110 may be connected with the processing device 120 directly as indicated by the bi-directional arrow in dotted lines linking the MR scanner and the processing device 120. As a further example, the storage device 130 may be connected with the processing device 120 directly (not shown in FIG. 1) or through the network 150. As still a further example, one or more terminal(s) 140 may be connected with the processing device 120 directly (as indicated by the bi-directional arrow in dotted lines linking the terminal(s) 140 and the processing device 120) or through the network 150.

The MR scanner 110 may scan a (part of) subject or locate within its detection region and generate MR signals relating to the (part of) subject. In the present disclosure, the terms "subject" and "object" are used interchangeably. In some embodiments, the subject may include a body, a substance, or the like, or a combination thereof. In some embodiments, the subject may include a specific portion of a body, such as the head, the thorax, the abdomen, or the like, or a combination thereof. In some embodiments, the subject may include a specific organ, such as the heart, the esophagus, the trachea, the bronchus, the stomach, the gallbladder, the small intestine, the colon, the bladder, the ureter, the uterus, the fallopian tube, etc. In some embodiments, the subject may include a region of interest (ROI) in the specific organ (e.g., a tumor). The MR scanner 110 may include a magnet assembly, a gradient coil assembly, and a radiofrequency (RF) coil assembly.

The magnet assembly may generate a first magnetic field (also referred to as a main magnetic field) for polarizing the subject to be scanned. The magnet assembly may include a permanent magnet, a superconducting electromagnet, a resistive electromagnet, etc. The gradient coil assembly may generate a second magnetic field (also referred to as a gradient magnetic field). The gradient coil assembly may include X-gradient coils, Y-gradient coils, and Z-gradient coils. The gradient coil assembly may generate one or more magnetic field gradient pulses to the main magnetic field in the X direction (Gx), Y direction (Gy), and Z direction (Gz) to encode the spatial information of the subject. In some embodiments, the X direction may be designated as a frequency encoding direction, while the Y direction may be designated as a phase encoding direction. In some embodiments, Gx may be used for frequency encoding or signal readout, generally referred to as frequency encoding gradient or readout gradient. In some embodiments, Gy may be used for phase encoding, generally referred to as phase encoding gradient. In some embodiments, Gz may be used for slice selection for obtaining 2D k-space data based on MR signals. Gz may be used for phase encoding for obtaining 3D k-space data based on MR signals.

The RF coil assembly may include a plurality of RF coils. The RF coils may include one or more RF transmit coils and/or one or more RF receiver coils. The RF transmit coil(s) may transmit RF pulses to the subject. Under the coordinated action of the main magnetic field, the gradient magnetic field, and the RF pulses, MR signals relating to the subject may be generated according to a pulse sequence. The RF receiver coils may acquire MR signals from the subject according to the pulse sequence. The pulse sequence may be defined by imaging parameters and arrangement associated with the image parameters in time sequence. Exemplary pulse sequences may include a spin echo sequence, a gradient echo sequence, a diffusion sequence, an inversion recovery sequence, or the like, or a combination thereof. For example, the spin echo sequence may include a fast spin echo (FSE), a turbo spin echo (TSE), a rapid acquisition with relaxation enhancement (RARE), a half-Fourier acquisition single-shot turbo spin-echo (HASTE), a turbo gradient spin echo (TGSE), or the like, or a combination thereof.

The MR signals may also be referred to as echo signals. The MR signals may be used to fill a k-space based on a sampling technique. Exemplary sampling techniques may include a Cartesian sampling technique, a spiral sampling technique, a radial sampling technique, a Z-sampling technique, an undersampling technique, etc. The received MR signal(s) may be sent to the processing device 120 directly or via the network 150 for image reconstruction and/or image processing. In some embodiments, the MR scanner 110 may include an analog-to-digital converter (ADC) (not shown in FIG. 1). The analog-to-digital converter may convert MR signals received by one or more RF receiver coils into digital data. The digital data may be used to fill a k-space to generate k-space data. The analog-to-digital converter may be a direct-conversion ADC, a successive-approximation ADC, a ramp-compare ADC, a Wilkinson ADC, an integrating ADC, a delta-encoded ADC, a pipeline ADC, a sigma-delta ADC, or the like, or a combination thereof.

The processing device 120 may process data and/or information obtained from the MR scanner 110, the terminal(s) 140, and/or the storage device 130. For example, the processing device 120 may obtain MR image data including a first intensity distribution of a first magnetic field relative to at least one portion of a first subject. The processing device 120 may also obtain a target machine learning model that provides a mapping relationship between intensity distributions of magnetic fields and corresponding susceptibility distributions associated with one or more subjects under one or more magnetic field. The target machine learning model may be configured to output a susceptibility distribution associated with a specific subject. The processing device 120 may determine a first susceptibility distribution associated with the first subject based on the mapping relationship using the target machine learning model. As another example, the processing device 120 may reconstruct a target MR image of the subject based on the first susceptibility distribution associated with the first subject. As still another example, the processing device 120 may obtain a plurality of training data. The processing device 120 may generate the target machine learning model by training a machine learning model (e.g., a neural network model) using the plurality of training data.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the MR scanner 110, the terminal(s) 140, and/or the storage device 130 via the network 150. As another example, the processing device 120 may be directly connected to the MR scanner 110, the terminal(s) 140 and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the terminal(s) 140 and/or the processing device 120. The data may include image data acquired by the MR scanner 110, image data acquired by the processing device 120, algorithms and/or models for processing the image data, etc. For example, the storage device 130 may store image data (e.g., MR signals, k-space data, an MR complex diagram, an MR phase diagram, an MR field diagram, etc.) acquired by the MR scanner 110. As another example, the storage device 130 may store one or more algorithms for processing the image data, a target machine learning model for generating susceptibility distribution, etc. In some embodiments, the storage device 130 may store data and/or instructions that the processing device 120 may execute or use to perform exemplary methods/systems described in the present disclosure. In some embodiments, the storage device 130 may include mass storage, removable storage, volatile read-and-write memory, read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the MRI system 100 (e.g., the processing device 120, the terminal(s) 140, etc.). One or more components in the MRI system 100 may access the data or instructions stored in the storage device 130 via the network 150. In some embodiments, the storage device 130 may be directly connected to or communicate with one or more other components in the MRI system 100 (e.g., the processing device 120, the terminal(s) 140, etc.). In some embodiments, the storage device 130 may be part of the processing device 120.

The terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may be part of the processing device 120.

In some embodiments, the terminal(s) 140 may send and/or receive information relating to MR image reconstruction to the processing device 120 via a user interface. In some embodiments, the user interface may be in form of an application for MR image reconstruction implemented on the terminal(s) 140. The user interface may be configured to facilitate communication between the terminal(s) 140 and a user associated with the terminal(s) 140. In some embodiments, the user interface may receive an input of a request for MR image reconstruction from the user through, for example, a user interface screen. The terminal(s) 140 may send the request for MR image reconstruction to the processing device 120 via the user interface. The processing device 120 may obtain MR image data of a subject and a target machine learning model as described elsewhere in the present disclosure from the MR scanner 110, and/or the storage device 130. The processing device 120 may further generate a susceptibility distribution associated with the subject and determine a target MR image of the subject based on the susceptibility distribution associated with the subject.

In some embodiments, the user interface may receive a signal from the processing device 120. The signal may include the target MR image generated by the processing device 120. In some embodiments, the signal may be further configured to cause the terminal(s) 140 to display the target MR image to the user.

The network 150 may include any suitable network that can facilitate the exchange of information and/or data for the MRI system 100. In some embodiments, one or more components of the MR scanner 110, the terminal(s) 140, the processing device 120, the storage device 130, etc., may communicate information and/or data with one or more other components of the MRI system 100 via the network 150. For example, the processing device 120 may obtain data from the MR scanner 110 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the assembly and/or function of the MRI system 100 may be varied or changed according to specific implementation scenarios.

Figure 2:
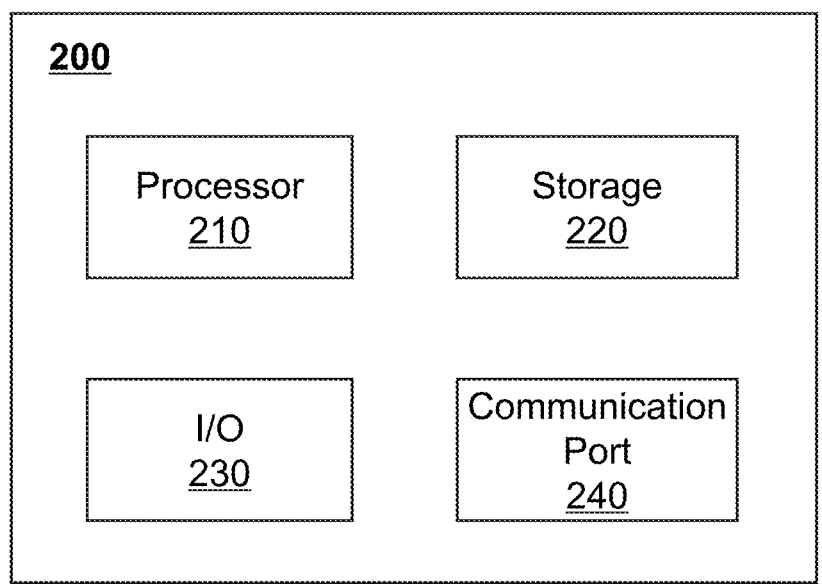
FIG. 2 is a schematic diagram illustrating hardware and/or software components of an exemplary computing device on which the processing device 120 may be implemented according to some embodiments of the present disclosure.

FIG. 2 is a schematic diagram illustrating hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 120 in accordance with techniques described herein. The computer instructions may include, for example, routines, programs, objects, components, signals, data structures, procedures, modules, and functions, which perform particular functions described herein. For example, the processor 210 may process data obtained from the MR scanner 110, the terminal(s) 140, the storage device 130, and/or any other component of the MRI system 100. Specifically, the processor 210 may process one or more measured data sets obtained from the MR scanner 110. For example, the processor 210 may reconstruct an image based on the data set(s). In some embodiments, the reconstructed image may be stored in the storage device 130, the storage 220, etc. In some embodiments, the reconstructed image may be displayed on a display device by the I/O 230. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the MR scanner 110, the terminal(s) 140, the storage device 130, or any other component of the MRI system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for reconstructing MR images.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the MR scanner 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the MRI system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
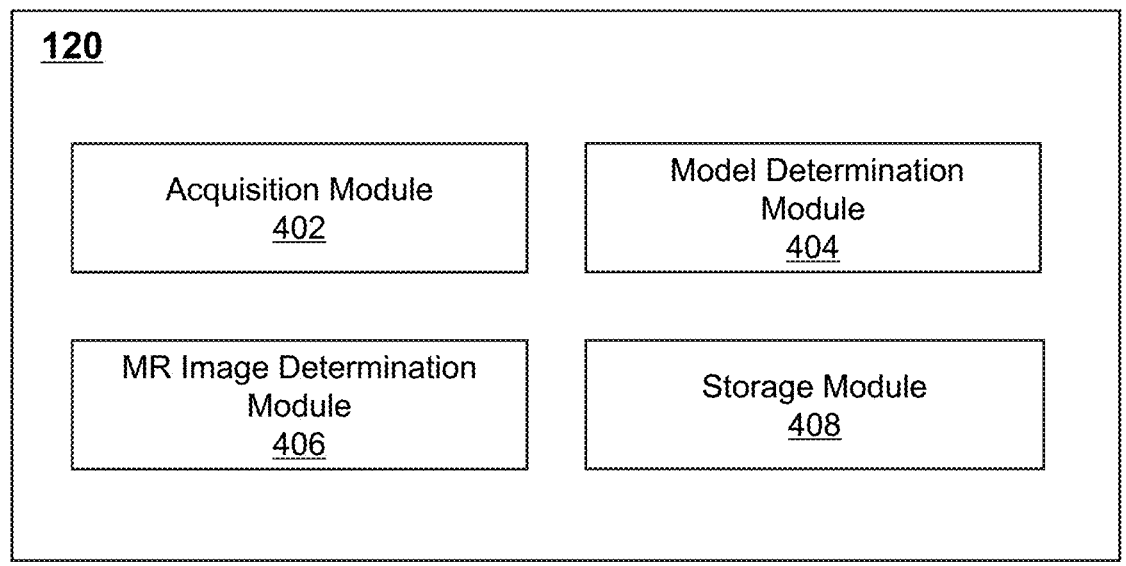
FIG. 4 is a block diagram illustrating an exemplary processing device according to some embodiments of the present disclosure.

FIG. 4 is a block diagram illustrating an exemplary processing device 120 according to some embodiments of the present disclosure. In some embodiments, the processing device 120 may be implemented on a computing device as illustrated in FIG. 2 or a mobile device as illustrated in FIG. 3. As illustrated in FIG. 4, the processing device 120 may include an acquisition module 402, a model determination module 404, an MR image determination 406, and a storage module 408. In some embodiments, the modules may be connected with each other via a wired connection (e.g., a metal cable, an optical cable, a hybrid cable, or the like, or any combination thereof) or a wireless connection (e.g., a Local Area Network (LAN), a Wide Area Network (WAN), a Bluetooth, a ZigBee, a Near Field Communication (NFC), or the like, or a combination thereof).

The acquisition module 402 may be configured to obtain information and/or data for generating an MR image. In some embodiments, the acquisition module 402 may be configured to obtain image data relating to one or more subjects. The image data may indicate an intensity distribution of a magnetic field associated with a subject. In some embodiments, the acquisition module 402 may be configured to obtain a target machine learning model that provides a mapping relationship between image data indicating the intensity distribution and a susceptibility distribution relating to the subject. The acquisition module 402 may transmit the information and/or data to other components of the processing device 120 for further processing. For example, the acquisition module 402 may transmit image data and a target machine learning model to the MR image determination module 406 to determine a susceptibility distribution associated with the subject.

The model determination module 404 may be configured to generate a target machine learning model. The target machine learning model may provide a mapping relationship between image data indicating the intensity distribution and a susceptibility distribution relating to a subject. The target machine learning model may be configured to output the susceptibility distribution relating to the subject when the image data are inputted into the target machine learning model based on the mapping relationship. The target machine learning model may be constructed based on a neural network model. Exemplary neural network models may include a back propagation (BP) neural network model, a radial basis function (RBF) neural network model, a deep belief nets (DBN) neural network model, an Elman neural network model, or the like, or a combination thereof. In some embodiments, the model determination module 404 may generate the target machine learning model by training the neural network model using a plurality of groups of training data relating to multiple samples. The model determination module 404 may transmit the target machine learning model to other components of the processing device 120 for further processing. For example, the model determination module 404 may transmit the target machine learning model to the MR image determination module 406 to determine the susceptibility distribution relating to the subject.

The MR image determination module 406 may be configured to generate a target MR image relating to a subject based on a susceptibility distribution associated with a subject. In some embodiments, the susceptibility distribution associated with the subject under a magnetic field may be generated by inputting the image data indecating the intensity distribution of the magnetic field into a target machine learning model. The target machine learning model may determine the susceptibility distribution associated with the subject under the magnetic field based on the mapping relationship between magnetic field intensity distribution and susceptibility distribution. Then the target machine learning model may be configured to output the susceptibility distribution associated with the subject. In some embodiments, the intensity distribution of the magnetic field (e.g., an MR field diagram) may be identified from the image data (e.g., an MR phase diagram). The intensity distribution of the magnetic field may be inputted into the target machine learning model. The susceptibility distribution associated with the subject may be generated and/or outputted by the target machine learning model based on the mapping relationship.

The storage module 408 may store information. The information may include programs, software, algorithms, data, text, number, images and some other information. For example, the information may include image data, an intensity distribution of a magnetic field, a susceptibility distribution associated with a subject, etc.

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. For instance, the assembly and/or function of the processing device 120 may be varied or changed according to specific implementation scenarios. Merely by way of example, the acquisition module 402 and the model determination module 404 may be integrated into a single module. As another example, some other components/modules may be added into the processing device 120. Such variations and modifications do not depart from the scope of the present disclosure.

Figure 5:
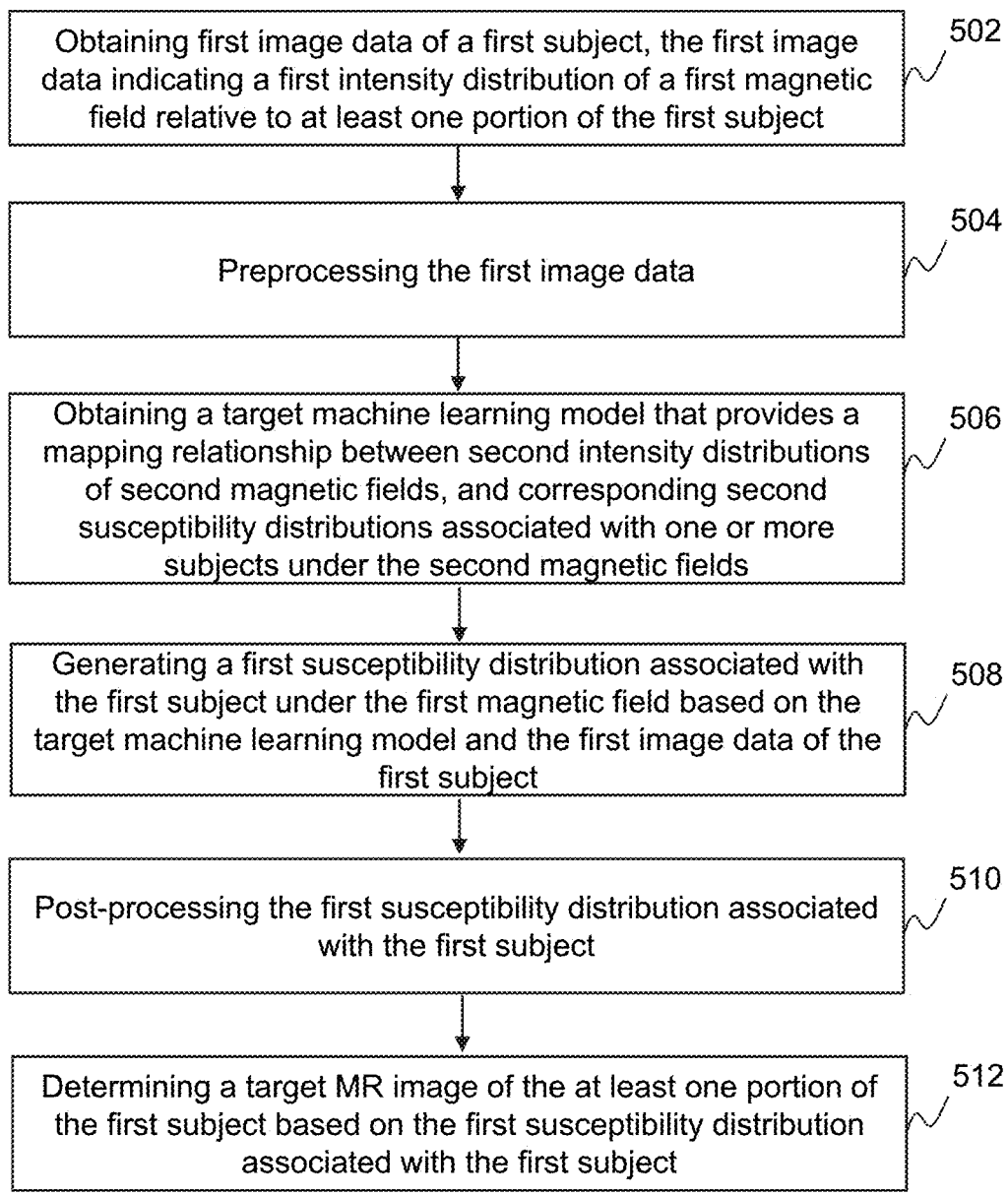
FIG. 5 is a flowchart illustrating an exemplary process for reconstructing an MR image according to some embodiments of the present disclosure.

FIG. 5 is a flowchart illustrating an exemplary process 500 for reconstructing an MR image according to some embodiments of the present disclosure. In some embodiments, one or more operations of the process 500 illustrated in FIG. 5 may be implemented in the MRI system 100 illustrated in FIG. 1. For example, process 500 illustrated in FIG. 5 may be stored in the storage device 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3).

In 502, first image data of a first subject may be obtained. Operation 502 may be performed by the acquisition module 402. The first subject may include substance, a sample (e.g., a phantom), a body, an organ and/or tissue of a body, etc. For example, the first subject may be the head, the chest, the lung, the pleura, the mediastinum, the large intestine, the small intestine, the bladder, the gallbladder, the triple burner, the pelvis, the backbone, the limbs, the skeleton, blood vessels, the neck, the thorax, the heart, the stomach, a soft tissue, a tumor, nodules, or the like, or any combination thereof as described elsewhere in the present disclosure (e.g., FIG. 1 and the descriptions thereof). The acquisition module 402 may obtain the first image data of the subject from the MR scanner 110, the storage device 130, the storage 220, the storage 390, or any other storage device. For example, the first image data may be obtained from the MR scanner 110 generated via scanning the first subject (e.g., a body or a phantom). As another example, the first image data may be obtained from the storage device 130 simulated by a processing device (e.g., the processing device 120) as described elsewhere in the present disclosure (e.g., FIGS. 6, 9A and 10A, and the descriptions thereof).

The first image data may indicate and/or include a first intensity distribution of a first magnetic field relative to at least one portion of the first subject. As used herein, an intensity distribution of a magnetic field relative to a specific subject may include a plurality of field intensities corresponding to different portions of the specific subject when the specific subject is under the magnetic field. The field intensities of the first magnetic field corresponding to different portions of the first subject (e.g., a body) may be different. For example, the head of a body may correspond to a larger field intensity than other portions of the body under the first magnetic field. As another example, the soft tissue of a body may correspond to a lower field intensity than other portions of the body under the first magnetic field.

In some embodiments, the first image data may include raw data (e.g., MR signals), k-space data, an MR complex diagram, an MR phase diagram, etc. The raw data (e.g., MR signals) may be obtained by encoding echo signals generated by using an MR scanner (e.g., MR scanner 110) scanning the first subject. For example, the first image data include high-frequency or low-frequency components of the MR signals associated with the first subject. The k-space data may be obtained by filling a k-space with MR signal samples generated by using a certain sampling technique. Exemplary sampling technique may include a line-by-line Cartesian algorithm, a spiral algorithm, a radial algorithm, a Zig-Zag algorithm, etc. The MR complex diagram and/or the MR phase diagram may be reconstructed based on the k-space data using an MR image reconstruction technique. Exemplary MR image reconstruction techniques may include a 2-dimensional Fourier transform technique, a back-projection technique (e.g., a convolution back projection technique, a filtered back projection technique), an iteration technique, etc. In some embodiments, the first image data may be the first intensity distribution of the first magnetic field relative to at least one portion of the first subject. For example, the first intensity distribution of the first magnetic field relative to at least one portion of the first subject may include an MR field diagram. The first intensity distribution of the first magnetic field relative to at least one portion of the first subject may be extracted and/or identified from the raw data, the k-space data, the MR complex diagram, the MR phase diagram, or the like, or a combination thereof.

The first image data may be two-dimensional (2D) image data, three-dimensional (3D) image data, etc. In some embodiments, the first image data may be in a time domain, or in a frequency domain, or in spatial domain, etc. For example, the first image data in the time domain may include raw data (e.g., MR signals). The first image data in the frequency domain may include k-space data. The first image data in the spatial domain may include an MR complex diagram, an MR phase diagram, an MR field diagram, or the like, or any combination thereof. In some embodiments, the first image data may be in an image field or in a data field. The first image data in the image field may refer to that the first image data is presented by an image or diagram. For example, the first image data in the image field may include an MR complex diagram, an MR phase diagram, etc. The first image data in the data field may refer to that the first data may be presented by data and/or information associated with elements of the first image data (e.g., values of pixels and/or voxels in the first image data).

The first image data presented in different domains may be converted from each other. For example, the first image data presented in time the domain (e.g., MR signals or echo signals) may be converted into the frequency domain (e.g., k-space data). The first image data presented in the frequency domain (e.g., k-space data) may be converted into the spatial domain (e.g., an MR complex diagram, an MR phase diagram, etc.). The first image data in the image field and data field may be also converted from each other. More descriptions for converting the first image data from a domain (or field) to another domain (or field) may be found in operation 504.

In 504, the first image data may be pre-processed. Operation 504 may be performed by the acquisition module 402 or the model determination module 404.

In some embodiments, the pre-processing operation may include a first domain transformation operation to transform the first image data from a first domain into a second domain. The first domain transformation operation may include a Fourier transform operation (e.g., a Fast Fourier transform operation, a Discrete Fourier transform operation), an inverse Fourier transform operation, a Fourier series, an inverse Fourier series, a Laplace transform operation, an inverse Laplace transform operation, a wavelet transform operation, an inverse wavelet transform operation or the like, or a combination thereof. The Fourier transform operation and/or the wavelet transform operation may be used to transform the first image data from the time domain and/or spatial domain into the frequency domain. For example, if the first image data includes MR signals in time domain, the MR signals in time domain may be transformed into MR spectrum data in the frequency domain using the Fourier transform operation and/or the wavelet transform operation. As another example, if the first image data includes an MR phase diagram, the MR phase diagram may be transformed from the spatial domain into the frequency domain using the Fourier transform operation. The Laplace transform operation may be performed to transform the first image data from the time domain into the complex frequency domain. For example, if the first image data includes MR signals in the time domain, the MR signals in the time domain may be transformed into the complex frequency domain using the Laplace transform operation. Specially, the MR signals may be decomposed into real part data and imaginary part data using the Laplace transform operation, which may be respectively filled into a k-space to form real part k-space data and imaginary part k-space data. As a further example, a real part image and an imaginary part image (i.e., MR complex diagram) may be determined based on the real part k-space data and the imaginary part k-space data through a Fourier transform operation. Based on the real part image and the imaginary part image, the MR phase diagram may be obtained.

The pre-processing operation may further include operations performed to adjust the quality of the first image data (e.g., MR signals, k-space data, an MR phase diagram, an MR field diagram. etc.), such as the noise level of an image, the contrast of an image, the artifact of an image, the resolution of an image, etc. In some embodiments, the pre-processing operation may include a denoising operation, an enhancement operation, a smoothing operation, a fusion operation, a segmentation operation, a registration operation, a transformation operation, or the like, or a combination thereof. Specifically, the smoothing operation may be performed based on a Gaussian filter, an average filter, a median filter, a wavelet transformation, or the like, or a combination thereof. The enhancement operation may include a histogram equalization, an image sharpening, a Fourier transform, a high-pass filtering, a low-pass filtering, or the like, or a combination thereof. The denoising operation may include applying a spatial-domain filter, a transform-domain filter, a morphological noise filter, or the like, or a combination thereof. The segmentation operation may be performed based on a segmentation algorithm. Exemplary segmentation algorithms may include a threshold-based segmentation algorithm, an edge-based segmentation algorithm, a region-based segmentation algorithm, or the like, or a combination thereof. The fusion operation may be performed using, for example, an optimal seam-line algorithm, a gradient pyramid algorithm, etc. The registration operation may be performed using, for example, a cross-correlation algorithm, a Walsh transform algorithm, a phase correlation algorithm, etc. The transformation operation may include an image geometric transformation, an image perspective transformation, an image affine transformation, etc.

In 506, a target machine learning model that provides a mapping relationship between second intensity distributions of second magnetic fields, and corresponding second susceptibility distributions associated with one or more second subjects under the second magnetic fields may be obtained. Operation 506 may be performed by the acquisition module 402 and/or the model determination module 404. The target machine learning model may be configured to output a susceptibility distribution associated with a specific subject under a magnetic field based on the mapping relationship by inputting image data of specific subject into the target machine learning model. The second subject may include a substance, a sample (e.g., a phantom), at least one specific portion of a body (e.g., an organ, and/or tissue of a patient), etc., as described elsewhere in the present disclosure. The one or more second subjects may be the same as or different from the first subject. For example, the first subject and the one or more second subjects may both be the head of a body. In some embodiments, the one or more second subjects may include the first subject. For example, the first subject may be a portion (e.g., ROI) of one of the one or more second subjects. The second magnetic fields may be same as or different from the first magnetic field. The second magnetic fields may include a high frequency magnetic field with a strong source, a high frequency magnetic field with a weak source, a low frequency magnetic field with a strong source, a low frequency magnetic field with a weak source, or the like, or any combination thereof.

In some embodiments, the acquisition module 402 may obtain the target machine learning model from the storage device 130, the storage 220, the storage 390, the storage module 408, or any other storage device. The target machine learning model may be pre-trained by the processing device 120 (e.g., the model determination module 404) and stored in the storage device 130, the storage 220, the storage 390, the storage module 408, or any other storage device. For example, the model determination module 404 may train a neural network model using a plurality of first groups of training data relating to multiple samples to obtain a first neural network model. The model determination module 404 may further determine the target machine learning model based on the first neural network model. In some embodiments, the model determination module 404 may designate the first neural network model as the target machine learning model, that may also be referred to as a general neural network model. In some embodiments, the model determination module 404 may train the first neural network model using a plurality of second groups of training data relating to the first subject to obtain a second neural network model. The second neural network model may be determined as the target machine learning model, that may also be referred to as a personalized neural network model.

Exemplary neural network models may include a back propagation (BP) neural network model, a radial basis function (RBF) neural network model, a deep belief nets (DBN) neural network model, an Elman neural network model, or the like, or a combination thereof. Each group of the plurality of first groups of training data may include second image data and a reference susceptibility distribution associated with a sample. A sample may include a third subject, such as a substance, a phantom, at least one specific portion of a body (e.g., an organ, and/or tissue of a patient), etc., as described elsewhere in the present disclosure. The multiple samples may be same as or different from the first subject. Each group of the plurality of second groups of training data may include third image data and a second reference susceptibility distribution associated with the first subject. During a training process of the neural network model, the mapping relationship between second intensity distributions of second magnetic fields, and corresponding second susceptibility distributions associated with second subjects under the second magnetic fields may be established. More descriptions for generating a target machine learning model may be found elsewhere in the present disclosure (e.g., FIG. 6 and FIG. 8, and the descriptions thereof).

In 508, a first susceptibility distribution associated with the first subject under the first magnetic field may be generated based on the target machine learning model and the first image data of the first subject. Operation 508 may be performed by the MR image determination module 406. The first susceptibility distribution associated with the first subject under the first magnetic field may present the distribution of susceptibilities relative to various portions or compositions of the first subject. In some embodiments, the first susceptibility distribution associated with the first subject under the first magnetic field may be generated by inputting the first image data of the first subject (the first image data obtained in 502 or the first image data in 504) into the target machine learning model. The target machine learning model may determine the first susceptibility distribution associated with the first subject under the first magnetic field based on the mapping relationship. Then the target machine learning model may be configured to output the first susceptibility distribution associated with the first subject under the first magnetic field. In some embodiments, the first intensity distribution of the first magnetic field (e.g., an MR field diagram) may be identified from the first image data (e.g., an MR phase diagram). The first intensity distribution of the first magnetic field may be inputted into the target machine learning model. The first susceptibility distribution associated with the first subject may be generated and/or outputted by the target machine learning model based on the mapping relationship.

Figure 11A:
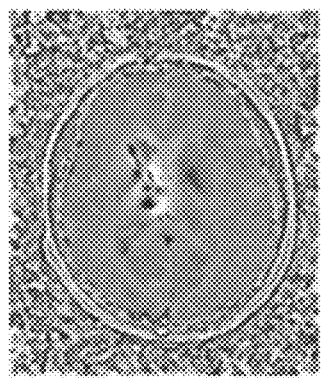
FIG. 11A and FIG. 11B are schematic diagrams illustrating exemplary features of a subject and reference subject according to some embodiments of the present disclosure.
Figure 11B:
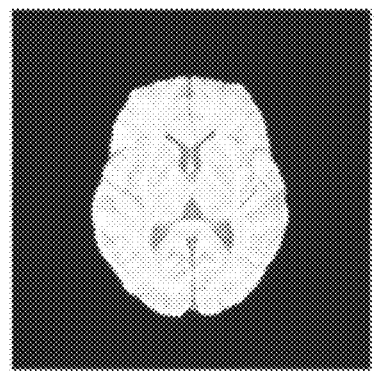

In some embodiments, the first susceptibility distribution associated with the first subject may be generated based on one or more constraint conditions. Exemplary constraint conditions may include a scanning parameter associated with the first image data, a forward dipole kernel function associated with the first image data, a feature relating to a reference subject around the first subject, a feature relating to the at least one portion of the first subject, or a spatial relationship between the first subject and the reference subject around the first subject. The scanning parameter associated with the first image data may include, for example, a direction of a scan plane, a scan positioning frame, parameters associated with a pulse sequence (e.g., an echo time, a flip angle associated with an RF pulse, etc.), etc. The forward dipole kernel function may be used to determine a field distribution based on a susceptibility distribution. The feature relating to the reference subject around the first subject may include the boundary, the shape, the size, the structure, etc., of the reference subject around the first subject. Exemplary reference subject may include the air around the first subject, tissues around the first subject, organs around the first subject, blood vessels around the first subject, or the like, or any combination thereof. For example, if the first subject is the nose of a body, the air in the nasal cavity may be the reference subject. The feature relating to the at least one portion of the first subject may include the shape, the size, the boundary, the structure, etc., of the at least one portion of the first subject (e.g., an ROI). The at least one portion of the first subject (e.g., an ROI) may include a tumor, a nodule, a hemorrhagic foci, or the like, or any combination thereof. For example, if the first subject is the stomach of a body, a tumor and/or a hemorrhagic foci in the stomach may be the at least one portion of the first subject. The spatial relationship between the first subject and the reference subject around the first subject may include the boundary relationship and the spatial location relationship between the reference subject and the first subject. The features of the first subject or reference subject around the first subject may be identified from an MR amplitude image (e.g., T1 mapping, T2 mapping, T2* mapping, etc.) of the first subject. For example, as shown in FIG. 11B, a boundary of the brain is profiled to distinguish the brain from around tissues.

In some embodiments, the first susceptibility distribution outputted by the target machine learning model may be in the time domain, or in the frequency domain, or in the spatial domain, etc. In some embodiments, the first susceptibility distribution may be in the image field or data field. For example, the first susceptibility distribution associated with the first subject under the first magnetic field may be a susceptibility map corresponding to the first subject in the image field. The susceptibility map corresponding to the first subject may include a 2D susceptibility map, a 3D susceptibility map, etc. The susceptibility map corresponding to the first subject may present the first subject based on a plurality of pixels or voxels. The susceptibilities relating to various portions or compositions of the first subject may be denoted by the colors of the plurality of pixels or voxels in the susceptibility map. In some embodiments, the first susceptibility distribution associated with the first subject under the first magnetic field may be denoted by a matrix (e.g., a 2D matrix, a 3D matrix, etc.) including a plurality of elements in the data field. One of the plurality of elements may represent a susceptibility of at least one portion or position of the first subject. The susceptibility of at least one portion or position of the first subject may be denoted by the value of a corresponding element in the matrix.

In 510, the first susceptibility distribution associated with the first subject may be post-processed. Operation 510 may be performed by the MR image determination module 406.

In some embodiments, the post-processing operation may include a second domain transformation operation to transform the first susceptibility distribution from a third domain into a fourth domain. Exemplary domain transformation operations may include a Fourier transform operation (e.g., a Fast Fourier transform operation, a Discrete Fourier transform operation), an inverse Fourier transform operation, a Fourier series, an inverse Fourier series, a Laplace transform operation, an inverse Laplace transform operation, a wavelet transform operation, an inverse wavelet transform operation or the like, or a combination thereof as described elsewhere in the present disclosure. In some embodiments, the post-processing operation may further include operations performed to adjust the quality of an image (such, MR image), such as the noise level of an image, the contrast of an image, the artifact of an image, the resolution of an image, etc. In some embodiments, the pre-processing operation may include a denoising operation, an enhancement operation, a smoothing operation, a fusion operation, a segmentation operation, a registration operation, a transformation operation, or the like, or any combination thereof as described elsewhere in the present disclosure.

In 512, a target MR image of the at least one portion of the first subject may be determined based on based on the first susceptibility distribution associated with the first subject. Operation 514 may be performed by the MR image determination module 406. In some embodiments, the target MR image of the at least one portion of the first subject may include the first susceptibility distribution generated in 508 (e.g., a susceptibility map). In some embodiments, the target MR image of the at least one portion of the first subject may include the post-processed first susceptibility distribution in 510.

It should be noted that the above description of the process magnetic resonance imaging is merely provided for the purposes of illustration, and not intended to limit the scope of the present disclosure. For persons having ordinary skills in the art, multiple variations and modifications may be made under the teachings of the present disclosure. For example, operation 502 and operation 504 may be performed simultaneously. As another example, process 500 may further include storing the first image data and the the first susceptibility distribution associated with the first subject. The first image data and the the first susceptibility distribution associated with the first subject may be used to update training data of the target machine learning model. As still a further example, operation 504, operation 510, and/or operation 512 may be omitted. In some embodiments, process 500 may further include identifying the first intensity distribution of the first magnetic field from the first image data. Such variations and modifications do not depart from the scope of the present disclosure.

FIG. 6 is a flowchart illustrating an exemplary process 600 of generating a machine learning model for magnetic resonance imaging according to some embodiments of the present disclosure. In some embodiments, one or more operations of the process 600 illustrated in FIG. 6 may be implemented in the MRI system 100 illustrated in FIG. 1. For example, the process 600 illustrated in FIG. 6 may be stored in the storage device 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3). Operation 506 may be performed according to process 600.

In 602, a plurality of first groups of training data associated with multiple first samples may be obtained. Operation 602 may be performed by the acquisition module 402 and/or the model determination module 404. Each of the plurality of first groups of training data may include first image data and a first reference susceptibility distribution associated with a first sample. The first image data associated with a first sample may indicate a first reference intensity distribution of a first reference magnetic field relative to at least one portion of the first sample. A first sample may include a substance, a phantom, a specific portion of a body (e.g., organ, and/or tissue of the patient), etc. For example, the first sample may be the head, the neck, the thorax, the heart, the stomach, a blood vessel, soft tissue, a tumor, nodules, or the like, or any combination thereof as described elsewhere in the present disclosure (e.g., FIG. 1 and the descriptions thereof). In some embodiments, the first reference magnetic field may be generated by an MR scanner (e.g., the MR scanner 110). In some embodiments, the first reference magnetic field may be simulated magnetic field (also referred to as virtual magnetic field).

In some embodiments, the first image data of a first sample may include raw data (e.g., MR signals), k-space data, an MR complex diagram, an MR phase diagram, etc., as described elsewhere in the present disclosure. In some embodiments, the first image data of a first sample may be the first reference intensity distribution of the first reference magnetic field relative to at least one portion of the first sample. For example, the first image data of the first sample may include an MR field diagram associated with the at least one portion of the first sample. The first reference intensity distribution of the first reference magnetic field relative to at least one portion of the first sample (e.g., an MR field diagram) may be extracted and/or determined from the raw data, the k-space data, the MR complex diagram, the MR phase diagram, or the like, or a combination thereof, associated with the at least one portion of the first sample. In some embodiments, the first image data of a first sample may be in a time domain, or in a frequency domain, or in a spatial domain, etc., as described elsewhere in the present disclosure (e.g., FIG. 5 and the descriptions thereof). In some embodiments, the first image data of a first sample may be in an image field or data field as described elsewhere in the present disclosure (e.g., FIG. 5 and the descriptions thereof).

In some embodiments, a first group of training data associated with a first sample may be obtained using an MR scanner (e.g., the MR scanner 110) via scanning the first sample. For example, the first image data of the first sample may be acquired by the MR scanner (e.g., the MR scanner 110) via scanning the first sample. The first reference susceptibility distribution associated with the first sample may be determined based on the corresponding first image data using a QSM technique. Exemplary QSM technique may include a single angle QSM algorithm, a multi-angle multi-scanning QSM algorithm, etc. The single angle QSM algorithm may include a truncated k-space division (TKD) algorithm, a weight k-space derivative (WKD) algorithm, Bayesian algorithm, etc. The multi-angle multi-scanning QSM algorithm may include a susceptibility tensor imaging (STI) algorithm, calculation of susceptibility through multiple orientation sampling (COSMOS) algorithm, etc.

In some embodiments, a first group of training data associated with a first sample may be obtained using a simulation technique based on a physical relationship between susceptibility distribution and field distribution defined by a dipole kernel function. The dipole kernel function may include a reverse dipole kernel function and a forward dipole kernel function. The reverse dipole kernel function may be used to determine a susceptibility distribution based on an intensity distribution of a magnetic field. The forward dipole kernel function may be used to determine an intensity distribution of a magnetic field based on a susceptibility distribution. Specially, an reference intensity distribution (i.e., the first image data) of a reference magnetic field (i.e., virtual magnetic field) in a first group may be simulated based on a reference susceptibility distribution associated with the subject according to a forward dipole model associated with the forward dipole kernel function, that is denoted by Equation (1) as below:

$$\Delta B(r) = B_0 \cdot F^{-1}\{g(k) \cdot \chi(k)\} \quad (1),$$

where, $\Delta B(r)$ denotes an intensity distribution of a magnetic field, $\chi(r)$ denotes a susceptibility distribution, $k=[k_x,k_y,k_z]$ refers to k-space coordinates, $r=[x,y,z]$ refers to image space coordinates, $B_0$ refers to an intensity of an external magnetic field, $F^{-1}$ refers to a reverse Fourier transform operator, and $g(k)$ refers to a forward magnetic dipole kernel function denoted by Equation (2) as below:

$$g(k) = \begin{cases} \dfrac{1}{3} - \dfrac{k_z^2}{k_x^2 + k_y^2 + k_z^2}, & k \neq 0 \\ 0, & k = 0 \end{cases} \quad (2)$$

Using the forward dipole model, the model determination module 404 may pre-determine a first reference susceptibility distribution associated with a first sample according to a default setting of the MRI system 100. Then the model determination module 404 may calculate the first reference intensity distribution of a reference magnetic field (i.e., virtual magnetic field) relative to at least one portion of the first sample by inputting the first reference susceptibility distribution associated with the first sample into Equation (1).

In 604, an objective function including a regularization configured to constrain the training of the machine learning model to converge the objective function may be obtained. Operation 604 may be performed by the acquisition module 402 and/or the model determination module 404. In some embodiments, the regularization configured to constrain the training of the machine learning model to converge the objective function may be constructed based on a scanning parameter associated with the first image data of the first sample, a forward dipole kernel function associated with the first image data of the first sample, a feature relating to a reference subject around the first sample, a feature relating to the at least one portion of the first sample, or a spatial relationship between the first sample and the reference subject around the first sample as described elsewhere in the present disclosure (e.g., FIG. 5 and the descriptions thereof). The scanning parameter associated with the first image data of the first sample may include a direction of a scan plane, a scan positioning frame, parameters associated with a pulse sequence used for scanning (e.g., an echo time, a flip angle associated with an RF pulse, etc.), etc. The forward dipole kernel function associated with the first image data of the first sample may be used as a constrain condition for the reason that the forward dipole kernel function is a non-underdetermined function, which means no information will miss in the process of calculating the intensity distribution of a magnetic field based on the susceptibility distribution using the forward dipole kernel function. Through the constraining of the forward dipole kernel function, the training process may be enhanced and accelerated, and the stability and accuracy of the machine learning model may be improved.

The feature relating to the reference subject around the first sample may include the boundary, the shape, the size, the structure, etc., of the reference subject around the first sample. For example, for the nasal cavity (i.e., ROI), when conducting a magnetic resonance imaging, air in the nasal cavity may be a noise source (also referred to a noise region or a background region). The intensity distribution of a magnetic field and the susceptibility distribution in the noise region or background region will not satisfy the dipole kernel function, which may be considered as a constraint for the training of the machine learning model.

The feature relating to the at least one portion of the first sample may include the shape, the size, the boundary, the structure, etc., of the at least one portion of the first sample (e.g., an ROI). For example, when conducting a magnetic resonance imaging of the brain, lesions (e.g., a tumor, a nodule, a hemorrhage point, etc.) in the brain may be a noise source with a low signal intensity or a high magnetic susceptibility, which may be considered as a constraint for the training of the machine learning model. As shown in FIG. 11A, a lesion with irregular boundary exists in the brain region. The irregular boundary of the lesion may be identified manually by a user.

In 606, a machine learning model may be trained using the plurality of first groups of training data based on the objective function to obtain a first machine learning model. Operation 606 may be performed by the model determination module 404. The machine learning model may be an artificial neural network (ANN) model including a back propagation (BP) neural network model, a convolutional neural network (CNN) model, a deep neural network (DNN) model, a radial basis function (RBF) neural network model, a deep belief nets (DBN) neural network model, an Elman neural network model, or the like, or a combination thereof. In some embodiments, the neural network model may include multiple layers, for example, an input layer, multiple hidden layers, and an output layer. The multiple hidden layers may include one or more convolutional layers, one or more batch normalization layers, one or more activation layers, a fully connected layer, a cost function layer, etc. Each of the multiple layers may include a plurality of nodes.

In some embodiments, the machine learning model may be defined by a plurality of parameters. Exemplary parameters of the machine learning model may include the size of a convolutional kernel, the number of layers, the number of nodes in each layer, a connected weight between two connected nodes, a bias vector relating to a node, etc. The connected weight between two connected nodes may be configured to represent a proportion of an output value of a node to be as an input value of another connected node. The bias vector relating to a node may be configured to control an output value of the node deviating from an origin.

In some embodiments, the machine learning model may be trained using at least one training algorithm. Exemplary training algorithm may include a gradient descent algorithm, a Newton's algorithm, a Quasi-Newton algorithm, a Levenberg-Marquardt algorithm, a conjugate gradient algorithm, or the like, or a combination thereof, as exemplified in FIG. 8 and the description thereof. In some embodiments, the neural network model may be trained by performing a plurality of iterations. Before the plurality of iterations, the parameters of the neural network model may be initialized. For example, the connected weights and/or the bias vector of nodes of the neural network model may be initialized to be random values in a range, e.g., the range from −1 to 1. As another example, all the connected weights of the neural network model may have a same value in the range from −1 to 1, for example, 0. As still an example, the bias vector of nodes in the neural network model may be initialized to be random values in a range from 0 to 1. In some embodiments, the parameters of the neural network model may be initialized based on a Gaussian random algorithm, a Xavier algorithm, etc. Then the plurality of iterations may be performed to update the parameters of the neural network model until a condition is satisfied. The condition may provide an indication of whether the neural network model is sufficiently trained. For example, the condition may be satisfied if the value of a cost function associated with the neural network model is minimal or smaller than a threshold (e.g., a constant). As another example, the condition may be satisfied if the value of the cost function converges. The convergence may be deemed to have occurred if the variation of the values of the cost function in two or more consecutive iterations is smaller than a threshold (e.g., a constant). As still an example, the condition may be satisfied when a specified number of iterations are performed in the training process.

For each of the plurality of iterations, first image data and a first reference susceptibility distribution associated with a first sample in one group of the plurality of first groups of training data may be inputted into the machine learning model. The first image data may be processed by one or more layers of the machine learning model to generate an estimated susceptibility distribution. The estimated susceptibility distribution may be compared with the first reference susceptibility distribution associated with the first sample based on the cost function of the machine learning model. The cost function of the machine learning model may be configured to assess a difference between a testing value (e.g., the estimated susceptibility distribution) of the neural network model and a desired value (e.g., the reference susceptibility distribution associated with the first sample). If the value of the cost function exceeds a threshold in a current iteration, the parameters of the neural network model may be adjusted and updated to cause the value of the cost function corresponding to the first image data (i.e., the difference between the estimated susceptibility distribution and the reference susceptibility distribution) smaller than the threshold. Accordingly, in a next iteration, another group of first image data and a first reference susceptibility distribution associated with the first sample may be inputted into the neural network model to train the neural network model as described above until the condition is satisfied.

In some embodiments, the model determination module 404 may further process the first machine learning model to generate a target machine learning model according to operations 608-612. In some embodiments, the model determination module 404 may perform the operation 614 directly to designate the first machine learning model as a target machine learning model.

In 608, a plurality of second groups of training data associated with a second sample may be obtained. Operation 608 may be performed by the acquisition module 402 and/or the model determination module 404. Each of the plurality of second groups of training data may include second image data and a second reference susceptibility distribution associated with a second sample. The second image data associated with the second sample may indicate a second reference intensity distribution of a second reference magnetic field relative to at least one portion of the second sample. The second sample (e.g., the first subject as described in FIG. 5) may include a substance, a phantom, a specific portion of a body (e.g., organ, and/or tissue of the patient), etc., as described elsewhere in the present disclosure. In some embodiments, the second reference magnetic field may be generated by an MR scanner (e.g., the MR scanner 110). In some embodiments, the second reference magnetic field may be a simulated magnetic field (also referred to as virtual magnetic field).

In some embodiments, the second image data associated with a second sample may include raw data (e.g. MR signals), k-space data, an MR complex diagram, an MR phase diagram, an MR field diagram, etc., as described elsewhere in the present disclosure.

In 610, the first machine learning model may be trained using the plurality of second groups of training data based on the objective function to obtain a second machine learning model. Operation 606 may be performed by the model determination module 404. The training process of the first machine learning model may be similar to or same as the training process described in the operation 606. The second machine learning model may also be referred to as a personalized machine learning model.

In 612, the second machine learning model may be determined as a target machine learning model. Operation 612 may be performed by the model determination module 404. The target machine learning model may provide a mapping relationship between the first image data (or intensity distribution of a magnetic field) and the susceptibility distribution. The second machine learning model may be configured to output a susceptibility distribution associated with a first subject based on the mapping relationship when the first image data associated with the first subject are inputted into the second machine learning model. In some embodiments, the second machine learning model may be determined based on the updated parameters. In some embodiments, the second machine learning model may be transmitted to the storage device 130, the storage module 408, or any other storage device for storage.

In some embodiments, the second machine learning model may be updated based on a testing performed on the target machine learning model. If the test result of the target machine learning model does not satisfy a condition, the target machine learning model may be updated. The target machine learning model may be tested based on one or more groups of test data. A group of test samples may include a test image data, and a reference susceptibility distribution. The test image data may be inputted into the target machine learning model to output a predicted susceptibility distribution. The susceptibility distribution may be compared with the reference susceptibility distribution. If the difference between the predicted susceptibility distribution and the reference susceptibility distribution is greater than a threshold, the test result of the target machine learning model is deemed not satisfying the condition, and the target machine learning model may need to be updated. The testing of the target machine learning model may be performed according to an instruction of a user, clinical demands, or a default setting of the MRI system 100. For example, the target machine learning model may be tested at set intervals (e.g., every other month, every two months, etc.). As another example, the target machine learning model may be updated based on added data in a training set of the target machine learning model over a period of time. If the quantity of the added data in the training set over a period of time is greater than a threshold, the target machine learning model may be updated based on the updated training set. Accordingly, the target machine learning model may adapt to a complex clinical situation and have improved robustness.

It should be noted that the above description of the process of allocating computing resources for medical applications in response to requests for performing the medical applications is merely provided for the purposes of illustration, and not intended to limit the scope of the present disclosure. For persons having ordinary skills in the art, multiple variations and modifications may be made under the teachings of the present disclosure. Such variations and modifications do not depart from the scope of the present disclosure. For example, operation 602 and operation 608 may be performed simultaneously. In some embodiments, the convergence may be deemed to have been occurred if the variation of the values of the cost function in two or more consecutive iterations is equal to a threshold (e.g., a constant). In some embodiments, operations 608-612 may be omitted.

Figure 7:
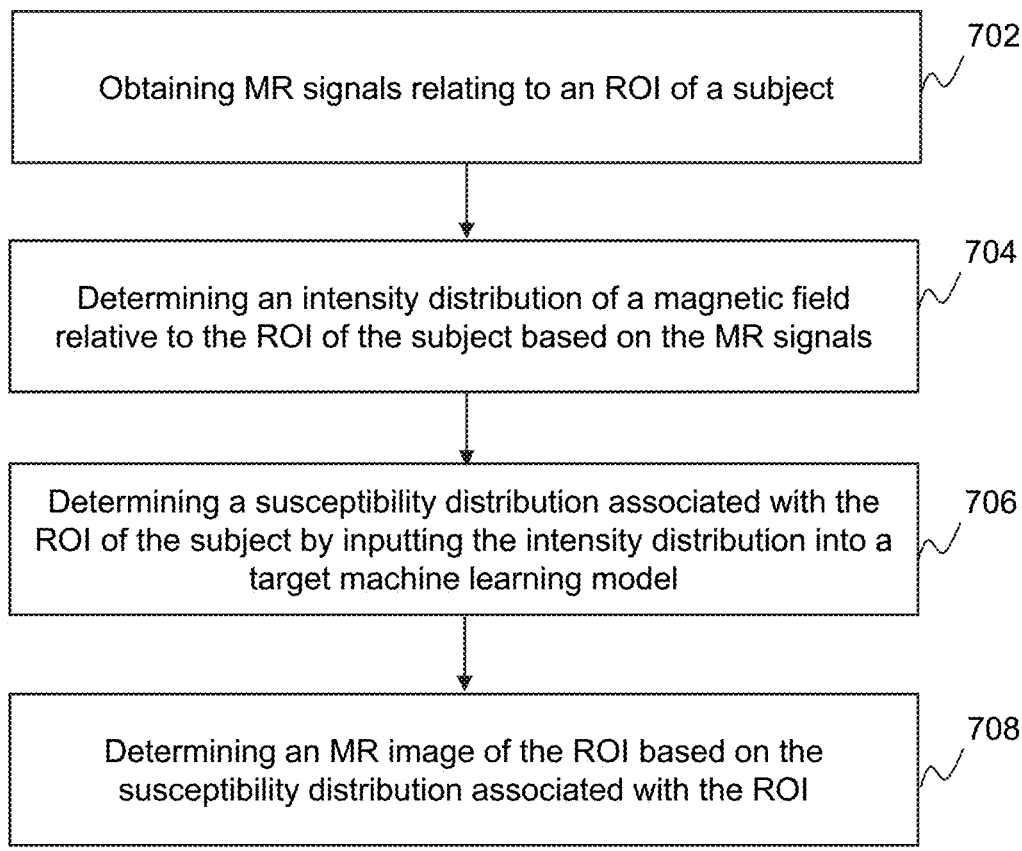
FIG. 7 is a flowchart illustrating an exemplary process for determining an MR image of the ROI according to some embodiments of the present disclosure.

FIG. 7 is a flowchart illustrating an exemplary process 700 for determining an MR image of the ROI according to some embodiments of the present disclosure. In some embodiments, one or more operations of the process 700 illustrated in FIG. 7 may be implemented in the MRI system 100 illustrated in FIG. 1. For example, the process 700 illustrated in FIG. 7 may be stored in the storage device 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3).

In 702, MR signals relating to an ROI of a subject may be obtained. Operation 702 may be performed by the acquisition module 402. The ROI of the subject may include substance, a phantom, a body, an organ and/or tissue of a body, etc., as described elsewhere in the present disclosure. In some embodiments, the MR signals may indicate an intensity distribution of a magnetic field relative to the ROI of the subject. The acquisition module 402 may obtain the MR signals relating to the ROI of the subject from the MR scanner, the storage device 130, the storage 220, the storage 390, or any other storage device. For example, the MR signals may be acquired by an MR scanner (e.g., the MR scanner 110) via scanning the ROI of the subject (e.g., a body or a phantom). As another example, the MR signals may be obtained from the storage device 130 simulated by a processing device (e.g., the processing device 120) as described elsewhere in the present disclosure (e.g., FIG. 9A and FIG. 10A and the descriptions thereof).

In 704, an intensity distribution of a magnetic field relative to the ROI of the subject may be determined based on the MR signals. Operation 704 may be performed by the MR image determination module 406. In some embodiments, for different ROIs, the intensity distribution of magnetic field relative to the ROI of the subject may be different. For example, for a brain tumor imaging, the ROI may be the brain of a patient corresponding to a magnetic field with a high intensity. As another example, for a knee meniscus imaging, the ROI may be the knee of a patient corresponding to a magnetic field with a low intensity.

The MR image determination module 406 may determine the intensity distribution of magnetic field based on the MR signals. For example, the MR signals may be decomposed into magnitude part and phase part. Based on the phase part image, the intensity distribution of magnetic field can be calculated.

In 706, a susceptibility distribution associated with the ROI of the subject under the magnetic field may be determined. Operation 706 may be performed by the MR image determination module 406. The susceptibility distribution associated with the ROI of the subject under the magnetic field may present the distribution of susceptibility relative to various portions or compositions of the ROI of the subject. In some embodiments, the susceptibility distribution associated with the ROI of the subject may be determined by inputting the intensity distribution into a target machine learning model. The target machine learning model may determine the susceptibility distribution of the magnetic field associated with the ROI of the subject under the magnetic field based on the mapping relationship. The target machine learning model may be configured to output the susceptibility distribution associated with the ROI of the subject. In some embodiments, the intensity distribution of first magnetic field (e.g., an MR field diagram) may be identified from the MR signals. The intensity distribution of the magnetic field may be inputted into the target machine learning model. The susceptibility distribution associated with the ROI of the subject may be generated and/or outputted by the target machine learning model based on the mapping relationship.

In some embodiments, the target machine learning model may be a trained neural network model. More descriptions for generating a target machine learning model may be found elsewhere in the present disclosure (e.g., FIG. 6 and FIG. 8, and the descriptions thereof).

In 708, an MR image of the ROI may be determined. Operation 706 may be performed by the MR image determination module 406. In some embodiments, the MR image determination module 406 may determine the MR image of the ROI based on the susceptibility distribution associated with the ROI using an MR image reconstruction technique. More descriptions of MR image reconstruction techniques may be found elsewhere in the present disclosure (e.g., FIG. 5 and the descriptions thereof).

It should be noted that the above description for the process of determining an MR image is merely provided for the purposes of illustration, and not intended to limit the scope of the present disclosure. For persons having ordinary skills in the art, multiple variations and modifications may be made under the teachings of the present disclosure. For example, operation 702 and operation 704 may be merged into one operation. As another example, process 700 may further include storing the MR signals and the susceptibility distribution associated with ROI of the subject. The MR signals and the susceptibility distribution associated with ROI of the subject may be used to update a training set of the target machine learning module. Process 700 may further include updating the target machine learning module based on the updated training set. Such variations and modifications do not depart from the scope of the present disclosure.

Figure 8:
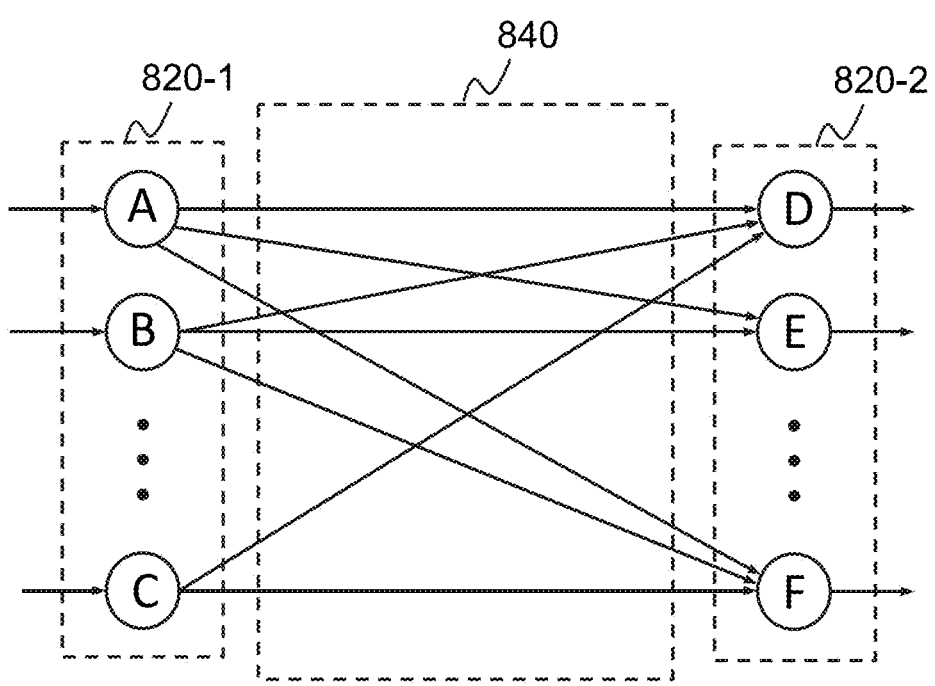
FIG. 8 is a schematic diagram illustrating an exemplary convolutional neural network (CNN) model according to some embodiments of the present disclosure.

FIG. 8 is a schematic diagram illustrating an exemplary neural network model according to some embodiments of the present disclosure.

A neural network model may include an input layer, one or more hidden layers, and an output layer. Each of the layers may include one or more nodes, also referred to as neurons. Neurons may be multi-input and single-output information processing unit with spatial integration and thresholding. The multiple hidden layers may include one or more convolutional layers, one or more Rectified Linear Units layers (ReLU layers), one or more pooling layers, one or more fully connected layers, or the like, or a combination thereof. As described in connection with process 600, the model determination module 404 may acquire image data including intensity distribution of a magnetic field as an input of the neural network model. The image data may be denoted by matrixes including a plurality of elements, respectively. A plurality of elements in a matrix may have a value (also referred to as pixel/voxel value) representing a characteristic of the element. Values of at least one portion of the plurality of elements in the image data may be inputted into the hidden layers.

For illustration purposes, as shown in FIG. 8, two-level neural network model is taken as an example. Hidden layers of the neural network model may include a convolutional layer 820-1 (also referred as a first level) and a pooling layer 820-2 (also referred as a second level). The convolutional layer 820-1 and the pooling layer 820-2 may by connected by a synapse network 840 connecting. The convolutional layer 820-1 may include a plurality of kernels (e.g., A, B, and C). The plurality of kernels may be used to extract image data of a subject. In some embodiments, each of the plurality of kernels may filter a portion (e.g., a region) of the image data of the subject to produce a specific feature or area corresponding to the portion (e.g., a region) of the image data. The feature may include a low-level feature (e.g., an edge feature, a texture feature), a high-level feature (e.g., a semantic feature), or a complicated feature (e.g., a deep hierarchical feature) that is calculated based on the kernel(s).

The pooling layer 820-2 may take the output of the convolutional layer 820-1 as an input. The pooling layer 820-2 may include a plurality of pooling nodes (e.g., D, E and F). The plurality of pooling nodes may be used to sample the output of the convolutional layer 820-1, and thus may reduce the computational load of data processing and increase the speed of data processing of the MRI system 100. In some embodiments, the model determination module 404 may reduce the volume of the matrix corresponding to image data in the pooling layer 820-2. For example, the model determination module 404 may divide the image data into multiple regions in the pooling layer 820-2. The average of values of pixels in one of the multiple regions may be designated as the value of a pixel representing the one of the multiple regions.

The synapse network 840 may include a plurality of synapses configured to connect the kernels included in the convolutional layer 820-1 with the pooling nodes included in the pooling layer 820-2. Each synapse may be configured with a weight, which may be randomly initialized to be a small number and updated during the training process. For example, the image data including the intensity distribution of the magnetic field may be taken as an input of the neural network model, and a predicated intensity distribution of the magnetic field may be outputted by the neural network model 800. A difference between the predicated intensity distribution and the reference intensity distribution of the magnetic field may be determined, and be sent back to each layer to updated the weight using a backpropagation pass algorithm.

It should be noted that the neural network model may be modified when applied in different conditions. For example, in a training process, a Rectified Linear Units layer may be added. An activation function may be used by the Rectified Linear Units layer to constrain an output of the Rectified Linear Units layer. Exemplary activation functions may include a linear function, a ramp function, a threshold function, a Sigmoid function, etc.

In some embodiments, the model determination module 404 may get access to multiple processing units, such as GPUs, in the MRI system 100. The multiple processing units may perform parallel processing in some layers of the neural network model. The parallel processing may be performed in such a manner that the calculations of different nodes in a layer of the neural network model may be assigned to two or more processing units. For example, one GPU may run the calculations corresponding to kernels A and B, and the other GPU(s) may run the calculations corresponding to kernels C and D in the convolutional layer 820-1. Similarly, the calculations corresponding to different nodes in another type of layers in the neural network model may be performed in parallel by the multiple GPUs.

EXAMPLE

The examples are provided for illustration purposes, and not intended to limit the scope of the present disclosure.

Figure 9A:
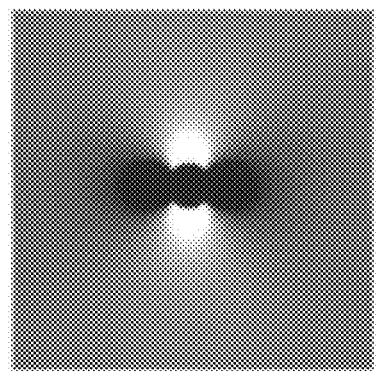
FIG. 9A and FIG. 9B are schematic diagrams illustrating exemplary simulated and real intensity distribution of a magnetic field according to some embodiments of the present disclosure.
Figure 9B:
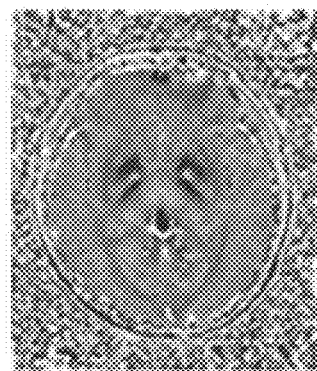

Example 1 Exemplary Intensity Distributions of a Magnetic Field Relative to the Head of a Body FIGS. 9A and 9B are exemplary images illustrating intensity distributions of a magnetic field relative to the head of a body according to some embodiments of the present disclosure. As shown in FIG. 9A, the intensity distribution of a magnetic field relative to the head of a body was simulated by a processing device as described in connection with FIG. 6. As shown in FIG. 9B, the intensity distribution of a magnetic field relative to the head of a body was generated by scanning the head of the body using an MR scanner (e.g., the MR scanner 110).

Example 2 Exemplary Susceptibility Distribution Relative to the Head of a Body

Figure 10A:
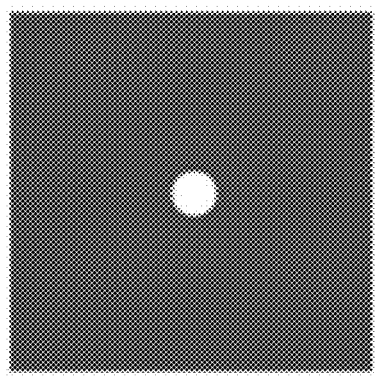
FIG. 10A and FIG. 10B are schematic diagrams illustrating exemplary simulated and real susceptibility distribution images according to some embodiments of the present disclosure.
Figure 10B:
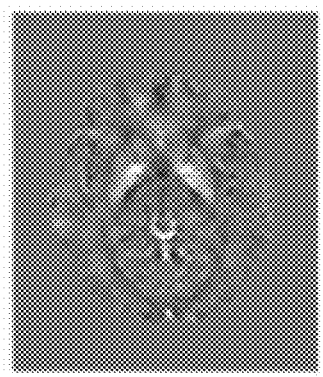

FIGS. 10A and 10B are exemplary images illustrating susceptibility distribution determined based on the intensity distributions in FIGS. 9A and 9B respectively according to some embodiments of the present disclosure. As shown in FIG. 10A, the susceptibility distribution relative to the head of the body was determined based on the simulated intensity distribution as shown in FIG. 9A. As shown in FIG. 10B, the susceptibility distribution relative to the head of the body was determined based on the intensity distribution as shown in FIG. 9B.

Example 3 Exemplary Susceptibility Distribution Relative to the Head of a Body

FIGS. 11A and 11B are exemplary images illustrating susceptibility distributions determined based on the intensity distributions in FIG. 9B according to some embodiments of the present disclosure. The susceptibility distribution relative to the head of the body in FIGS. 11A and 11B were determined based on the intensity distribution as shown in FIG. 9B using a target neural network model as described in elsewhere in the present disclosure. The susceptibility distribution in FIG. 11A was further determined using the target neural network model based on a constraint condition, such as a boundary of a focus in the head. The susceptibility distribution in FIG. 11B was further determined using the target neural network model based on a constraint condition, such as a boundary of the brain in the head.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques.

Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system for magnetic resonance imaging (MRI), comprising:
   at least one storage device storing executable instructions, and
   at least one processor in communication with the at least one storage device, when executing the executable instructions, causing the system to:
      obtain first image data of a first subject, the first image data indicating a first intensity distribution of a first magnetic field relative to at least one portion of the first subject;
      obtain a target machine learning model that provides a mapping relationship between second intensity distributions of second magnetic fields and corresponding second susceptibility distributions associated with second subjects under the second magnetic fields;

generate a first susceptibility distribution associated with the first subject under the first magnetic field based on the target machine learning model and the first image data of the first subject; and determine a target MR image of the at least one portion of the first subject based on the first susceptibility distribution associated with the first subject.

2. The system of claim 1, wherein the first image data includes at least one of an MR complex diagram, an MR phase diagram, or an MR field diagram.

3. The system of claim 1, wherein to generate a first susceptibility distribution associated with the first subject under the first magnetic field based on the target machine learning model and the first image data of the first subject, the at least one processor is further configured to cause the system to:

input the first image data of the first subject into the target machine learning model; and obtain the first susceptibility distribution associated with the first subject outputted by the target machine learning model based on the mapping relationship.

4. The system of claim 1, wherein to generate a first susceptibility distribution associated with the first subject under the first magnetic field based on the target machine learning model and the first image data of the first subject, the at least one processor is further configured to cause the system to:

identify the first intensity distribution of the first magnetic field from the first image data;

input the first intensity distribution of the first magnetic field into the target machine learning model; and obtain the first susceptibility distribution associated with the first subject outputted by the target machine learning model based on the mapping relationship.

5. The system of claim 1, wherein the at least one processor is further configured to cause the system to:

perform a domain transformation operation on at least one of the first image data of the first subject or the first susceptibility distribution associated with the first subject.

6. The system of claim 5, wherein the at least one processor is further configured to cause the system to:

perform a first domain transformation operation on the first image data of the first subject; and perform a second domain transformation operation on the first susceptibility distribution associated with the first subject, the second domain transformation operation being a reverse operation of the first domain transformation operation.

7. The system of claim 1, wherein the at least one processor is further configured to cause the system to:

generate the first susceptibility distribution associated with the first subject based on the mapping relationship and at least one of a scanning parameter associated with the first image data, a dipole kernel function associated with the first image data, a feature relating to a reference subject around the first subject, a feature relating to the at least one portion of the first subject, or a spatial relationship between the first subject and the reference subject around the first subject.

8. The system of claim 1, wherein to obtain a target machine learning model, the at least one processor is further configured to cause the system to:

obtain a plurality of first groups of training data, each group of the plurality of first groups of training data including second image data and a first reference susceptibility distribution associated with a third subject, the second image data indicating a third intensity distribution of a third magnetic field relative to the third subject;

train a machine learning model based on the plurality of first groups of training data to obtain a first machine learning model; and determine the target machine learning model based on the first machine learning model.

9. The system of claim 8, wherein to train a machine learning model based on the plurality of first groups of training data, the at least one processor is further configured to cause the system to:

for each group of the plurality of first groups of training data, identify the third intensity distribution of the third magnetic field from the second image data; and train the machine learning model using the identified third intensity distribution of the third magnetic field and the first reference susceptibility distribution associated with the third subject corresponding to the each group of the plurality of first groups of training data.

10. The system of claim 8, wherein to determine the target machine learning model based on the first machine learning model, the at least one processor is further configured to cause the system to:

obtain a plurality of second groups of training data, each group of the plurality of groups of training data including third image data and a second reference susceptibility distribution associated with the first subject;

train the first machine learning model using the plurality of second groups of training data to obtain a second machine learning model; and designate the second machine learning model as the target machine leaning model.

11. The system of claim 8, wherein to obtain a plurality of first groups of training data, the at least one processor is further configured to cause the system to:

for each of one or more groups of the plurality of first groups of training data, determine one or more first reference susceptibility distributions associated with the third subject;

simulate the second image data based on the corresponding first reference susceptibility distributions; and determine the one or more groups of the plurality of first groups of training data based on the one or more first reference susceptibility distributions and the simulated second image data.

12. The system of claim 8, wherein to train a machine learning model based on the plurality of first groups of training data, the at least one processor is further configured to cause the system to:

obtain an objective function including a regularization configured to constrain the training of the machine learning model to converge the objective function; and perform a plurality of iterations based on the objective function using the plurality of first groups of training data.

13. The system of claim 12, wherein the regularization is constructed based on at least one of a scanning parameter associated with the second image data, a dipole kernel function associated with the second image data, a feature relating to a reference subject around the third subject, a feature relating to the at least one portion of the third subject, or a spatial relationship between the third subject and the reference subject around the third subject.

14. A method implemented on a computing device including a storage device and at least one processor for magnetic resonance imaging, the method comprising:
- obtaining first image data of a first subject, the first image data indicating a first intensity distribution of a first magnetic field relative to at least one portion of the first subject;
- obtaining a target machine learning model that provides a mapping relationship between second intensity distributions of second magnetic fields and corresponding second susceptibility distributions associated with second subjects under the second magnetic fields;
- generating a first susceptibility distribution associated with the first subject under the first magnetic field based on the target machine learning model and the first image data of the first subject; and
- determining a target MR image of the at least one portion of the first subject based on the first susceptibility distribution associated with the first subject.

15. The method of claim 14, wherein the generating, based on the target machine learning model and the first image data of the first subject, a first susceptibility distribution associated with the first subject under the first magnetic field comprising:
- inputting the first image data of the first subject into the target machine learning model; and
- obtaining the first susceptibility distribution associated with the first subject outputted by the target machine learning model based on the mapping relationship.

16. The method of claim 14, wherein the generating a first susceptibility distribution associated with the first subject under the first magnetic field based on the target machine learning model and the first image data of the first subject comprising:
- identifying the first intensity distribution of the first magnetic field from the first image data;
- inputting the first intensity distribution of the first magnetic field into the target machine learning model; and
- obtaining the first susceptibility distribution associated with the first subject outputted by the target machine learning model based on the mapping relationship.

17. The method of claim 14, further comprise:
- performing a domain transformation operation on at least one of the first image data of the first subject or the first susceptibility distribution associated with the first subject.

18. The method of claim 14, further comprise:
- generating the first susceptibility distribution associated with the first subject based on the mapping relationship and at least one of a scanning parameter associated with the first image data, a dipole kernel function associated with the first image data, a feature relating to a reference subject around the first subject, a feature relating to the at least one portion of the first subject, or a spatial relationship between the first subject and the reference subject around the first subject.

19. The method of claim 14, wherein the obtaining the target machine learning model comprising:
- obtaining a plurality of first groups of training data, each group of the plurality of first groups of training data including second image data and a first reference susceptibility distribution associated with a third subject, the second image data indicating a third intensity distribution of a third magnetic field relative to the third subject;
- training a machine learning model based on the plurality of first groups of training data to obtain a first machine learning model; and
- determining the target machine learning model based on the first machine learning model.

20. A non-transitory computer readable medium storing instructions, the instructions, when executed by at least one processor, causing the at least one processor to implement a method comprising:
- obtaining first image data of a first subject, the first image data indicating a first intensity distribution of a first magnetic field relative to at least one portion of the first subject;
- obtaining a target machine learning model that provides a mapping relationship between second intensity distributions of second magnetic fields and corresponding second susceptibility distributions associated with second subjects under the second magnetic fields;
- generating a first susceptibility distribution associated with the first subject under the first magnetic field based on the target machine learning model and the first image data of the first subject; and
- determining a target MR image of the at least one portion of the first subject based on the first susceptibility distribution associated with the first subject.

* * * * *